(12) United States Patent
Naegerl

(10) Patent No.: US 7,938,862 B2
(45) Date of Patent: May 10, 2011

(54) ARTIFICIAL JOINT AND A JOINT PART INTENDED FOR THIS PURPOSE

(75) Inventor: Hans Naegerl, Gleichen (DE)

(73) Assignee: Aequos Endoprothetik GmbH, Graefelfing (DE)

( * ) Notice: Subject to any disclaimer, the term of this patent is extended or adjusted under 35 U.S.C. 154(b) by 301 days.

(21) Appl. No.: 12/187,879

(22) Filed: Aug. 7, 2008

(65) Prior Publication Data

US 2009/0048680 A1    Feb. 19, 2009

(30) Foreign Application Priority Data

Aug. 7, 2007    (DE) .......................... 10 2007 037 154

(51) Int. Cl.
*A61F 2/38*    (2006.01)
(52) U.S. Cl. ................ 623/20.21; 623/20.24; 623/20.27
(58) Field of Classification Search ..... 623/20.14–20.36
See application file for complete search history.

(56) References Cited

U.S. PATENT DOCUMENTS

| | | | | |
|---|---|---|---|---|
| 4,215,439 | A | * | 8/1980 | Gold et al. ................. 623/20.26 |
| 4,216,549 | A | * | 8/1980 | Hillberry et al. ........... 623/20.26 |
| 5,358,527 | A | * | 10/1994 | Forte ......................... 623/20.27 |
| 6,120,543 | A | | 9/2000 | Kubein-Meesenburg et al. |
| 6,235,060 | B1 | | 5/2001 | Kubein-Meesenburg et al. |
| 6,264,697 | B1 | * | 7/2001 | Walker ....................... 623/20.27 |
| 2004/0024325 | A1 | | 2/2004 | Nishibayashi et al. |
| 2004/0243245 | A1 | | 12/2004 | Plumet et al. |

FOREIGN PATENT DOCUMENTS

| | | |
|---|---|---|
| DE | 3908958 | 9/1990 |
| DE | 19521597 | 12/1996 |
| DE | 19646891 | 5/1998 |
| DE | 69623861 T2 | 1/2003 |
| EP | 0346183 A1 | 12/1989 |
| EP | 0600806 | 6/1994 |
| EP | 0734700 | 10/1996 |
| EP | 0749734 A1 | 12/1996 |
| WO | 9208424 A1 | 5/1992 |
| WO | 98/46171 A1 | 10/1998 |

\* cited by examiner

*Primary Examiner* — Corrine M McDermott
*Assistant Examiner* — Megan Wolf
(74) *Attorney, Agent, or Firm* — Leydig, Voit & Mayer, Ltd.

(57) ABSTRACT

An artificial joint as an endoprosthesis for a human joint, including a first joint part having two first functional surfaces, a second joint part having two second functional surfaces, the two first and second functional surfaces of each joint part being convex-concave, concave-convex, or convex-convex in a proximal-distal direction, a projection associated with the first joint part; and a recess associated with the second joint part. The recess is configured to engage with the projection so as to determine a relative position of the first and second joint parts in a transverse plane of the joint and to form a stop for a sliding movement of the first and second joint parts relative to each other. The two first functional surfaces are pivotable about a pivot axis with respect to the second functional surfaces.

13 Claims, 3 Drawing Sheets

ARTIFICIAL JOINT AND A JOINT PART INTENDED FOR THIS PURPOSE

Priority is claimed to German Patent Application No. DE 10 2007 037 154.5, filed Aug. 7, 2007, the entire disclosure of which is incorporated by reference herein.

The invention relates to an artificial joint as an endoprosthesis for a human joint, in particular a knee joint, consisting of at least two joint parts, each joint part comprising two functional surfaces, the two functional surfaces of each joint part being formed so as to be spheroidal and to be convex-concave, concave-convex, or convex-convex in the proximal-distal arrangement and the functional surfaces being pivotable about one pivot axis in each case, and being formed in such a way that upon extension/flexion of the joint a combination of a rolling and a sliding movement occurs, the artificial joint having a shaping which is formed by a projection associated with the first joint part and a recess associated with the second joint part and which determines the relative position of the two joint parts in the transverse plane and also forms a stop for a sliding movement of the joint parts relative to one another. The invention further relates to a joint part which is intended for use in an artificial joint of this type.

BACKGROUND

An artificial joint of this type may for example serve as an endoprosthesis for the human knee joint, which because of the incongruence of its osseous partners—the femoral condyle, tibial plateau and patella rear surface—requires a secondary stabilisation means. As passively acting structures, the secondary stabilisers include the capsuloligamentous apparatus and the menisci as well as the osseous portions. The muscles and tendons actively contribute to the stability. These secondary stabilisers delimit the extent of movement of the joint. The resulting degree of stability is of particular importance for the knee joint.

The extension/flexion of the joint represents the main plan of movement and is a combination of a rolling and a sliding movement of the femoral condyle over the tibial plateau. The front and rear cruciate ligament together form the central pillar of the knee joint. They stabilise the rolling and sliding movement of the knee joint and prevent the joint surfaces from sliding against one another.

Sudden uncontrolled twisting movements of the knee joint, which are not supported by the musculature, can lead to tearing of the cruciate ligaments. In most cases it is the front cruciate ligate that is affected, injuries to the rear cruciate ligament being rather rare.

In practice, a surgical cruciate ligament replacement procedure is often required in cases of this type. In this case, internal anchoring of a cruciate ligament replacement tendon is often undertaken in the joint, with an operating method involving little trauma. Through a small cut on the tibial plateau, the tendon of an adductor muscle is separated from the muscle under the skin with a special instrument.

This tendon, which is approximately 30 cm long, is then folded on top of itself four times, resulting in a replacement tendon for the cruciate ligament. This tendon must be introduced into the joint anatomically correctly in the place of the torn cruciate ligament. For this purpose, drilled channels through the tibial plateau and the thigh bone are produced with the help of aiming devices. The tendon is then drawn into the joint through the two drilled channels. There are various methods for stably fixing the tendon in the bone channel. The decision as to which method is to be used depends on individual anatomical properties of the patient, such as the length and thickness of the tendon.

A conventional joint which is configured as a knee joint prosthesis is described, for example, in DE 696 23 861 T2, in which a central rib, which is associated with the tibial joint part, engages in a cavity of the femoral joint part. In the extended position the wall of the cavity lies against the front side of the rib. There thus results a stop which is effective only in the extended position, i.e. in a single position.

A joint is described, for example, from EP 07 34 700 A 2. In this document, the joint geometry of the functional surfaces relative to one another is determined in each of the two planes by a joint chain with two joint axes, which extend through the centres of rotation of the functional surfaces with the radii of the respectively associated cross-sections, a connection which is on the femoral side, and thus on the condyle side, of the central points of the condyles corresponding to a frame, and a connection which is on the tibial side, and thus on the joint socket side, of the central points of the joint sockets corresponding to a connecting rod of a ligament chain comprising the four axes.

An artificial joint, in particular an endoprosthesis for the replacement of natural joints, consisting of at least two artificial joint parts with curved articulation surfaces, is described in DE 196 46 891 A1, a curved contact line being formed on each of the articulation surfaces. The curved contact line of one of the articulation surfaces is a portion of an elliptical cross-section of a first cylinder or cone with the cylinder radius or the cone angle. The other contact line occurs as a counter track of a second cylinder or second cone, with the cylinder radius or with the cone angle, rolling or sliding on the first cylinder or first cone. The articulation surfaces comprise control surfaces formed from a plurality of straight touch lines. These control surfaces are mutually attached to the contact lines lying opposite one another and the touch lines are in each case the connection lines between an instantaneous contact point of the contact lines and an instantaneous common point of the instantaneous pole of the respective movement systems in a reference plane or a reference sphere in the moved or unmoved system.

DE 195 21 597 A1 also relates to an artificial joint, in particular an endoprosthesis for the replacement of natural joints, consisting of at least two artificial joint parts with curved articulation surfaces, an arc-shaped contact line being formed on each of the articulation surfaces and in each case being a partial portion of a contact circle which lies in a plane and has a centre point. The articulation surfaces are arranged relative to one another as a pair, in such a way that the contact lines can roll on one another, and axes which extend perpendicular to the plane of the contact circles through the centre point thereof intersect at an intersection point. On one side, on the contact lines, control surfaces, which are formed from a plurality of straight touch lines, are formed, the touch lines lying on instantaneous connection lines of the instantaneous contact points, which occur during the rolling motion, with the instantaneous intersection points, which result from a pivoting movement of the contact lines at an angular speed around a common tangent of the contact lines through the instantaneous contact points.

EP 600 806 A1 even describes a knee prosthesis in three parts, with a femoral and a tibial implant, the femoral implant having an indentation, which circumscribes two condyle support saddles, which extend apart from one another and are connected by a trochlea, the femoral implant having a shape which results from the combination of the following features: that namely the inner and the outer condyle saddle have different radii of curvature in the sagittal plane, the bearing and sliding surfaces of the inner and outer condyle saddle have differences in width and cross-section in the frontal plane, the inner and outer condyle saddle have differences in rolling amplitude in the rear part, the trochlea delimits a surface with the cross-section of a geometric torus in the frontal and sagittal plane, said trochlea being raised on the outer side in an anatomical manner, the span of the bearing and sliding surfaces of the condyle saddle is increased in comparison to the anatomical ratios, and the condyle saddles are flattened, in order to promote the distribution of pressure.

An artificial joint which is intended to replace of human joints is known from the German patent application DE 39 08 958 A 1 and consists of two joint parts with movable functional surfaces. The ratios of curvature of the functional surfaces which have a circular cross-section are convex-convex, convex-concave, or concave-concave relative to one another, and the joint geometry is determined by a joint chain with two joint axes (dimer joint chain), which extends through the centres of rotation of the functional surfaces. In this case, the joint surfaces are formed so as to be spherical, in such a way that joint movement with five degrees of freedom is possible.

SUMMARY OF THE INVENTION

An aspect of the present invention is to provide the possibility of producing an artificial joint which in addition to the joint function which is known per se also performs partial functions of the ligamentous apparatus, in particular of the cruciate ligament. A further or alternate aspect of the invention is to provide an artificial joint part for use in an artificial joint of this type.

In accordance with one embodiment of the invention, there is provided an artificial joint, in which a respective posterior position in the sagittal plane is determined as a function of the angular position of the joint parts, in such a way that posterior sliding, in particular of the distal joint part, is delimited to a predetermined extent or excluded in each angular position. In this way, posterior displacement of a joint part is limited or prevented and the function of the rear cruciate ligament is anatomically correctly replaced in a simple way for each bending position. A progress distance which is defined by the rolling motion can advantageously also be used for determining the posterior position if the recess and the projection also determine a predetermined posterior position or delimited displaceability in each bending position, and thus in particular posterior displacement of the joint part which is associated with the tibia is excluded or limited to a particular amount. In addition, the shaping together with the engaging projection in the initial stage of bending can also take on the function of the front cruciate ligament, in such a way that additional auxiliary means are not required for joint stabilisation. In this case, the stability region of the natural ligamentous apparatus determines the tolerance in terms of the relative displaceability of the projection relative to the shaping.

In this case, it is particularly advantageous if the extent of a possible posterior displacement is determined and/or adjustable as a function of the loss of the natural ligamentous apparatus. In this way a comparatively large posterior displacement is thus dispensed with in practice if incorrect functioning of the movement path can be substantially avoided or eliminated by the natural ligamentous apparatus. For this purpose the gap between the recess and the projection is thus dimensioned so as to be comparatively large when the natural ligamentous apparatus is present to a large extent. For example, if the lateral tendons are lost, strict guidance can be provided by a narrow gap between the recess and the projection, up to the point of a constraint prosthesis construction.

A particularly advantageous embodiment of the present invention is achieved in that a posterior stop, dependent on the flexion angle of the joint, for the joint part which is associated with the tibia is formed by the shaping, in such a way as reliably to limit or to prevent the posterior displacement. The shaping in this case also delimits displacement towards the rear of the joint which is associated with the tibia, as well as a sliding movement which is undesired in this flexion position.

Moreover, it is also particularly expedient in accordance with a further embodiment of the present invention if the posterior position is constant independently of the flexion angle in the region of a relative sliding movement of the two joint parts. In this way, in contrast with the rolling phase, which is desired in the initial flexion stage and in which a particular posterior position is associated with a particular flexion angle by means of the cooperation of the recess with the projection, a variable flexion angle is made possible without the posterior relative position of the two joints being altered.

When the flexion angle is altered, posterior blocking could be achieved in discrete steps. On the other hand, however, it is particularly promising if the alteration of the posterior position is determined in particular linearly as a function of the flexion angle of the joint parts in the region of a relative rolling movement. In this way, a determined posterior position of the joint part which is associated with the tibia is thus achieved for each flexion angle. The bending movement is thus in no way compromised by the posterior blocking.

A particularly promising embodiment of the present invention is achieved in that the recess or the projection has a lateral extension or width which decreases towards the rear in the transverse plane, in such a way that because of the rolling movement of the joint parts, the projection which is in particular associated with the tibia engages in the recess which is in particular associated with the femur. The rolling movement consequently decreases the lateral extension, i.e. the width of the recess, in such a way that displacement is made possible only by virtue of the relative angular position of the joint parts.

The shaping could be provided in the shape of a drop, tail, or bead. However, it is also particularly simple for the shaping in the transverse plane to have a projection which is configured in the manner of a dovetail connection and which in particular has straight flanks, in order thus to achieve secure guidance, which requires only small alterations of the artificial joint according to the invention as compared with joints which are known per se. In particular, the mode of operation to be achieved as regards the rolling and sliding movement can thus be combined with the shaping without difficulty.

In this case, it is particularly expedient if the recess is formed between the convex functional surfaces of the joint part which is in particular associated with the femur, in such a way, for example, that even different joint parts can be combined, and may optionally form a shaping, in such a way that in the case of appropriate indication, a joint part can be subsequently replaced at a comparatively low expense.

In principle, the artificial joint produced in this way is suitable for replacing of various human joints. However, a particularly promising application involves the projection being associated with the tibial joint part and the recess being associated with the femoral joint part, in such a way that the projection and the recess can both be provided between the two functional surfaces of the same joint part. This is achieved, for example, by means of a portion in the shape of a drop and a tail, with guide grooves, of the inner inclines of the femoral joint parts, and by means of a corresponding, drop-shaped, horizontal and obliquely adapted vertical deformation of the joint part which is associated with the tibia.

A further particularly expedient development is achieved in that one of the joint parts has an in particular groove-shaped recess, in which a projection of the other joint part engages, in such a way as to prevent the functional surfaces of various joint parts being raised.

In this case it is also advantageous if the projection or the recess of at least one of the joint parts can be fixed to the joint so as to be exchangeable or replaceable, thus allowing it to be adapted optimally to various, in particular changing requirements. In an embodiment, the projection and the recess are separable from the corresponding first or second joint parts so as to be replaceable. Thus, if for example posterior blocking is not desired, a different joint part, which does not have the corresponding recess or the corresponding projection, can be provided without difficulty.

The present invention also provides an artificial joint with a projection or a recess for use in an artificial joint discussed above, which if required may also serve, for example, to replace an individual joint part of a previously introduced artificial joint. In this case, for example, the joint part which is associated with the femur can be combined with various joint parts which are associated with the tibia, and which can be introduced as a function of the respective indication.

BRIEF DESCRIPTION OF THE DRAWINGS

Various embodiments of the invention are possible. In order further to clarify the basic principle of the invention, one of these embodiments will be disclosed in the following and is shown in the drawings, in which.

DETAILED DESCRIPTION

Figure 1:
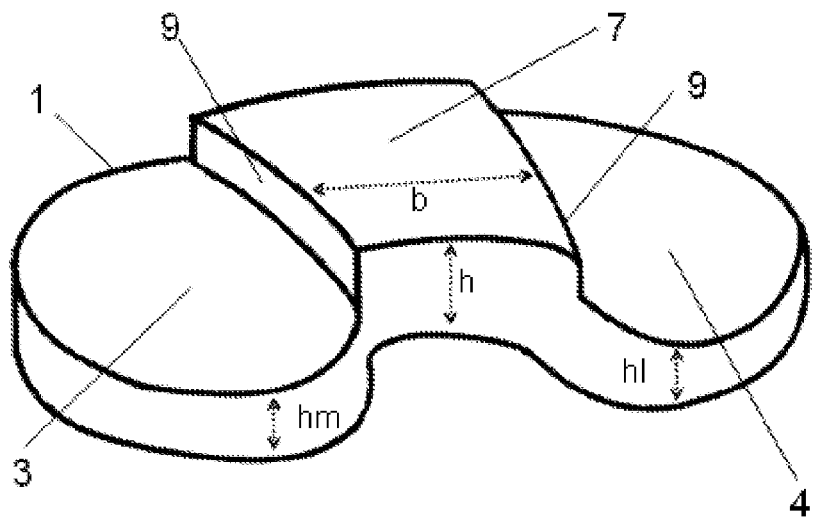
FIG. 1 is a perspective view of a tibial joint part with two functional surfaces which enclose a projection.
Figure 2:
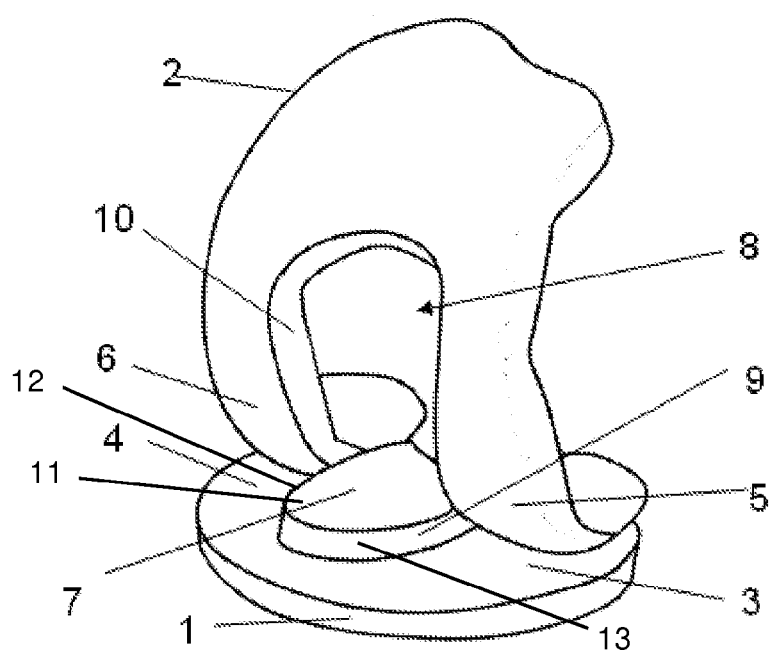
FIG. 2 is a perspective view of an arrangement of the tibial joint part which is shown in FIG. 1 and a femoral joint part in a highly bent position.
Figure 3:
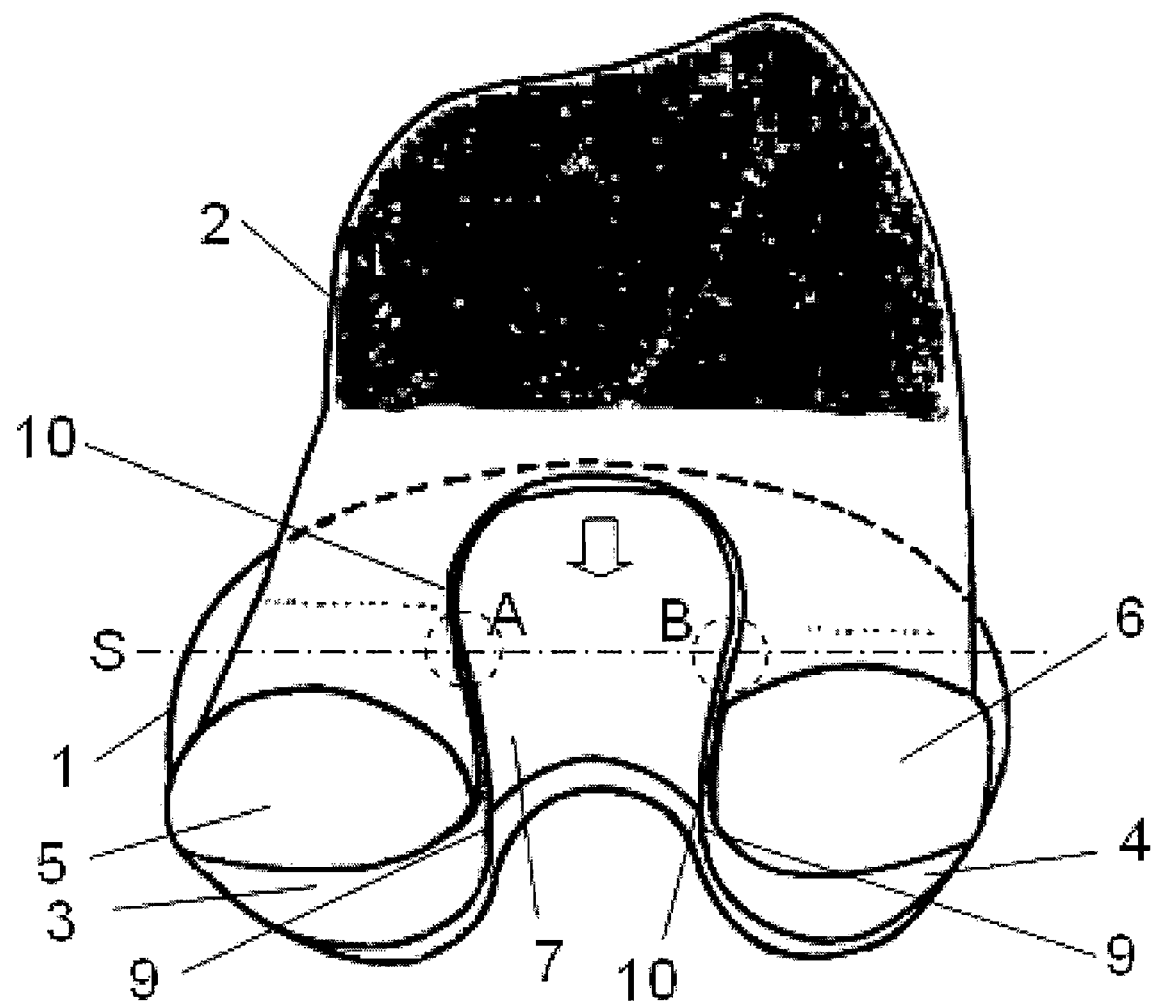
FIG. 3 is a rear view from diagonally above of an arrangement of the tibial and femoral joint parts, which are shown in FIG. 2, in an extended position.

The artificial joint according to the invention will be explained in greater detail in the following by way of FIGS. 1 to 5, FIG. 1 showing a perspective view of a tibial joint part 1 and FIG. 2 showing a perspective view of an arrangement of the tibial joint part 1 and a femoral joint part 2 as an endoprosthesis for a human knee joint in a highly bent position. Each joint part 1 comprises two functional surfaces 3, 4, each of which cooperates with a functional surface 5, 6 of the other joint part 2, the two functional surfaces 3, 4, 5, 6 of each joint part 1, 2 being formed so as to be spheroidal and convex-concave, concave-convex, or convex-convex in the proximal-distal arrangement. The functional surfaces 3, 4, 5, 6 are formed in such a way that upon extension/flexion of the joint, a combination of a rolling and a sliding movement occurs. In order to provide, in each bending position, a posterior blocking means which corresponds to the rear cruciate ligament, and moreover to allow in this state a posterior and also an anterior blocking means corresponding with the function of the front cruciate ligament, at a low bending angle of up to 10°, the artificial joint has a shaping, which is formed by a projection 7, associated with the first joint part 1, and by a recess 8, associated with the second joint part 2. By virtue of this shaping, the relative position of the two joint parts 1, 2 in the transverse plane is determined, and moreover a stop is formed for a sliding movement of the joint parts relative to one another. For this purpose, the recess 8 and the projection 7 comprise in the transverse plane a lateral extension which decreases towards the rear in the manner of a rounded-off dovetail connection 11 having straight flanks 12, 13. The recess 8 and the projection 7 each comprise a contact line 9, 10, on which at least two contact points acting as a posterior blocking means occur as a function of the flexion or on which at least two contact points acting as a posterior blocking means occur as a function of the flexion upon the posterior displacement of the joint parts 1, the contact points enclosing between them a distance b as a function of the flexion. Because of the difference of the height h of the projection 7 from the height hm of the functional surface 3 and the height hl of the functional surface 4, the functions of the lateral tendons may also be provided or supported.

In addition, the figure shows an arrangement of the tibial and femoral joint parts 1, 2 shown in FIG. 2, in an extended position in a rear view from diagonally above. As can clearly be seen, slipping of the tibial joint part 1 in relation to the femoral joint part 2 is excluded because of the conical shape of the contact line 9, formed on the side face, of the tibial joint part 1 on the projection 7 and of the contact line 10 of the femoral joint part 2. By this means, an undesired displacement of the functional surfaces 3, 4, 5, 6 is avoided.

Figure 4:
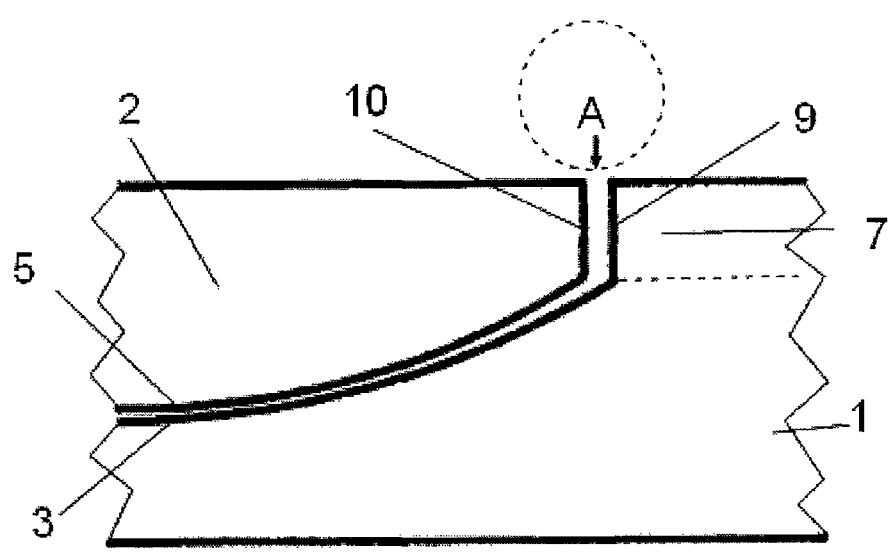
FIG. 4 is an enlarged sectional view of a detail of a side face A of the tibial and femoral joint parts from FIG. 3.
Figure 5:
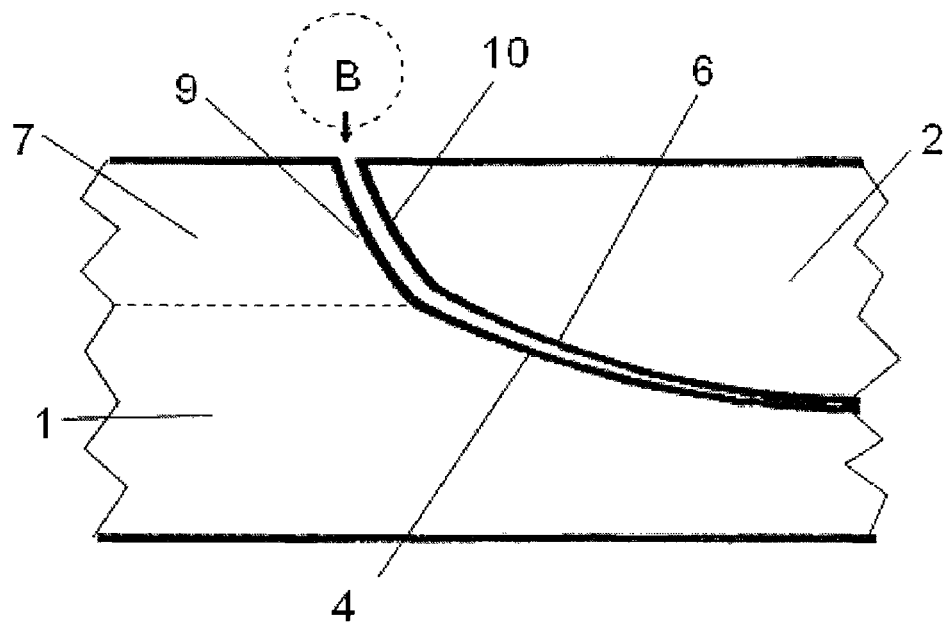
FIG. 5 is an enlarged sectional view of a detail of a side face B of the tibial and femoral joint parts from FIG. 3.

Possible embodiments of the contact line 9, formed on the side faces A and B, of the tibial joint part 1 on the projection 7 along the sectional line S perpendicular to the surface of the tibial joint part 1 and of the contact line 10 of the femoral joint part 2 are also additionally shown in FIGS. 4 and 5, which show a respective enlarged detail of the joint parts 1, 2 in a sectional view. The perpendicular course of the side face A relative to the surface of the tibial joint part 1 can also be seen in FIG. 4. By contrast, the side face B has a rounded-off configuration between the contact line 9 of the projection 7 on the tibial joint part 1 and the contact line 10 of the femoral joint part 2, and this can also be seen from FIG. 5.

What is claimed is:

1. An artificial joint as an endoprosthesis for a human joint, comprising:
    a first joint part having two first functional surfaces;
    a second joint part having two second functional surfaces, the two first and second functional surfaces of each joint part being convex-concave, concave-convex, or convex-convex in a proximal-distal direction;
    a projection associated with the first joint part; and
    a recess associated with the second joint part and configured to engage with the projection so as to determine a relative position of the first and second joint parts in a transverse plane of the joint depending on an angular position of the first and second joint parts,
    wherein the two first functional surfaces are pivotable about a pivot axis with respect to the second functional surfaces,
    wherein each of the first functional surfaces rolls and slides with respect to the second functional surfaces during an extension or flexion of the artificial joint,
    wherein the projection and recess form a posterior stop having a position depending on a flexion angle of the joint and configured to delimit or prevent a posterior sliding movement of at least one of the first and the second joint parts, and wherein the recess and the projection each include a width that decreases in a posterior direction in the transverse plane.

2. The artificial joint as recited in claim 1, wherein the human joint is a knee joint.

3. The artificial joint as recited in claim 2, wherein the projection is associated with a tibial joint part and the recess is associated with a femoral joint part.

4. The artificial joint as recited in claim 1, wherein a position of each of the first and the second joint part relative to one another is configured to be adjusted relative to a loss of ligament function in the human joint.

5. The artificial joint as recited in claim 1, wherein the position is constant in a region of a relative sliding movement of the first and second joint part.

6. The artificial joint as recited in claim 1, wherein the position is adjusted as a function of a flexion angle of the first and second joint parts in a region of a relative rolling movement of the first and second joint parts.

7. The artificial joint as recited in claim 1, wherein the projection is configured as a dovetail connection including straight flanks.

8. The artificial joint as recited in claim 1, wherein the second joint part is associated with a femur, the two second functional surfaces are convex, and the recess is disposed between the two second functional surfaces.

9. The artificial joint as recited in claim 1, wherein the projection is disposed between the two first functional surfaces.

10. The artificial joint as recited in claim 1, wherein the first joint part is a associated with a tibia.

11. The artificial joint as recited in claim 1, wherein the recess is shaped as a groove.

12. The artificial joint as recited in claim 1, wherein the projection and the recess are separable from the corresponding first or second joint parts so as to be replaceable.

13. The artificial joint as recited in claim 1, wherein at least one of the first joint part and the second joint part is fixable with respect to a human joint so as to be replaceable.

* * * * *